United States Patent [19]

Bauer, Jr. et al.

[11] Patent Number: 5,358,611

[45] Date of Patent: Oct. 25, 1994

[54] METHOD OF REDUCING IMPURITIES IN AQUEOUS MONOMER SOLUTIONS

[75] Inventors: William Bauer, Jr., Huntingdon Valley; Nelson I. Quirós, North Wales, both of Pa.

[73] Assignee: Rohm and Haas Company, Philadelphia, Pa.

[21] Appl. No.: 61,873

[22] Filed: May 17, 1993

[51] Int. Cl.$^5$ ................................. C07C 57/07
[52] U.S. Cl. ................... 204/157.093; 203/8; 203/DIG. 21; 204/158.21; 562/600
[58] Field of Search ............ 203/8, DIG. 21; 204/157.15, 158.2, 158.21, 157.93; 562/600

[56] References Cited

U.S. PATENT DOCUMENTS

| | | | |
|---|---|---|---|
| 3,203,169 | 8/1965 | D'Alelio | 204/157.15 |
| 3,725,208 | 4/1973 | Maezawa et al. | 203/DIG. 21 |
| 3,893,895 | 7/1975 | Dehnert et al. | 203/DIG. 21 |
| 3,894,923 | 7/1975 | Grégoire | 204/157.93 |
| 4,029,622 | 6/1977 | Keller et al. | 522/175 |
| 4,167,464 | 9/1979 | George | 522/182 |
| 4,294,676 | 10/1981 | Boutin et al. | 522/173 |
| 4,358,347 | 11/1982 | Mettetal et al. | 203/91 |
| 4,857,204 | 8/1989 | Joklik | 204/157.15 |
| 5,208,370 | 5/1993 | Bauer et al. | 562/600 |

FOREIGN PATENT DOCUMENTS

| | | |
|---|---|---|
| 102642 | 3/1984 | European Pat. Off. . |
| 41614 | 12/1974 | Japan . |
| 45219 | 1/1984 | Japan . |
| 4505 | 12/1985 | Japan . |
| 218556 | 9/1986 | Japan . |
| 0469416 | 5/1976 | U.S.S.R. ........... 204/158.21 |

*Primary Examiner*—Virginia Manoharan
*Attorney, Agent, or Firm*—David T. Banchik

[57] ABSTRACT

A method of reducing the levels of impurities in aqueous monomer solutions is provided. Subjecting aqueous monomer solutions to ultraviolet radiation for from about 2 minutes to about 5 hours, reduces the level of impurities, especially carbonyl-compounds.

10 Claims, No Drawings

METHOD OF REDUCING IMPURITIES IN AQUEOUS MONOMER SOLUTIONS

The present invention is directed to a method of reducing impurities in aqueous monomer solutions. In particular, the present invention is directed to a method of reducing the level of carbonyl-compounds in aqueous monomer solutions where one or more carbonyl-compounds are present as impurities.

In the production of certain monomers, ethylenically unsaturated hydrocarbons are oxidized, usually in the presence of a suitable catalyst to form the desired monomer. For example, one method for producing acrylic acid is by vapor-phase oxidation of propylene or acrolein in the presence of a catalyst. Similarly, methacrylic acid can be produced by vapor-phase oxidation of isobutylene, tert-butyl alcohol, tertiary-butyl methyl ether, methacrolein or isobutyrlaldehyde. The products which result from these processes are aqueous solutions of monomer which are contaminated with undesirable by-products. The aqueous monomer solutions are then extracted with a suitable solvent to recover the monomer. The organic phase containing the monomer is then stripped of the solvent in a solvent-separation step to obtain the monomer product. The low-boiling impurities are then distilled from the monomer product. Finally, the monomer product is distilled to separate high-boiling impurities.

Some of the impurities in the monomer product include carbonyl-compounds such as acrolein, methacrolein, acetaldehyde, furfural, protoanemonin, formaldehyde, crotonaldehyde, acetone and benzaldehyde. These by-products, or impurities, can impart color to the product or can act as polymerization inhibitors. Additional processing steps are required to reduce or remove these impurities, thereby increasing the cost of manufacturing pure monomer products.

Three general approaches have emerged for reducing the level of carbonyl-compounds in aqueous monomer systems: treating the aqueous monomer solution resulting from the vapor-phase oxidation, treating the extracted monomer/solvent mixture, and treating the glacial monomer. Generally, the treatments involve one or more distillations or the addition of one or more selectively reactive chemical agents.

A representative method of reducing by-products by treating an aqueous monomer solution is described in Japanese patent 62-045219. The method disclosed therein requires treating an aqueous acrylic acid solution with bisulfite, such as an alkali metal bisulfite or ammonium bisulfite before performing the extraction. Japanese patent 62-045219 discloses that this method is effective for reducing the levels of certain low-boiling impurities, including some carbonyl-containing compounds, present in the aqueous acrylic acid solution.

A representative method of reducing by-products by treating an extracted monomer/solvent mixture, is described in European patent application 102642. The method disclosed therein requires treating an extracted methacrylic acid/solvent mixture with an aqueous bisulfite solution, such as an alkali metal bisulfite or ammonium bisulfite, followed by a separation step.

Japanese patent application 61-218556 discloses a method of treating either an extracted acrylic acid/solvent mixture or a glacial acrylic acid to lower the levels of impurities. Japanese patent 64-004505 discloses a method of treating either an extracted methacrylic acid/solvent mixture or a glacial methacrylic acid to lower the levels of impurities. These references disclose that after the addition of bisulfite which is introduced into the aqueous monomer solution, the addition of hydrazine compounds to the extracted monomer/solvent mixture or to the glacial monomer, further reduces the levels of low-boiling impurities, including some carbonyl-containing compounds, present in the monomer product.

Japanese patent 81-41614 discloses a method of reducing the level of protoanemonin in acrylic acid by treating either the aqueous acrylic acid solution resulting from the vapor-phase oxidation, the extracted acrylic acid/solvent mixture, or the glacial acrylic acid. The method disclosed therein requires the addition of 0.5% to 1% by weight of the solution to which it is being added of a nitrous acid salt, nitrogen oxide or nitrosobenzene, and a polymerization inhibitor.

U.S. Pat. No. 3,725,208 is directed to a method of treating glacial acrylic acid to reduce the levels of aldehyde impurities. This patent discloses that the addition of sulfuric acid, hydrazine, phenylhydrazine, aniline, monoethanolamine, ethylenediamine or glycine to glacial acrylic acid followed by a distillation results in a reduction in the level of aldehyde impurities in the acrylic acid.

U.S. Pat. No. 3,893,895 is directed to a method of treating glacial 1,2-unsaturated carboxylic acids to reduce the level of carbonyl compounds which are present as impurities. The carbonyl compounds include acrolein, formaldehyde, methacrolein, crotonaldehyde, acetaldehyde, acetone and furfural.

According to the disclosure of the U.S. Pat. No. 3,893,895, the levels of these compounds in the 1,2-unsaturated carboxylic acids are reduced by treating the glacial acid with an amine and distilling the mixture. The amines which are disclosed as being useful are inorganic amines, primary and secondary aliphatic and aromatic amines, such as hydrazine, hydroxylamine, 1,2-ethanolamine, 1,2-ethylenediamine, octyl amine, 1,3-propanolamine, 1,2-propanolamine, octadecyl amine, aniline, p-phenylenediamine, o-phenylenediamine, 1,2-dianilinoethane, alpha naphthyl amine, beta naphthyl amine, p-methyl aniline, o-methyl aniline, N-methyl aniline, semi-carbazide, phenyl hydrazine, and 2,4-dimethyl aniline.

The methods of the prior art require the use of chemical additives as a means for reducing the level of impurities present therein. This approach may increase the cost and complexity of the purification process, may result in contaminating the product with other impurities, and may necessitate further purification steps. The present invention seeks to overcome the problems of the prior art.

In a first aspect of the present invention, there is provided a method of reducing the level of impurities in an aqueous monomer solution, comprising: subjecting the aqueous monomer solution containing the impurities to ultraviolet radiation for from about 2 minutes to about 5 hours.

The method of the present invention is preferably used to reduce the level of impurities such as, for example, carbonyl-compounds. Carbonyl-compounds present in aqueous monomer solutions include, for example, acrolein, methacrolein, acetaldehyde, furfural, protoanemonin, formaldehyde, crotonaldehyde, acetone and benzaldehyde. Preferably, the method of the present invention is used to reduce the level of furfural, protoanemonin and benzaldehyde.

The aqueous monomer solutions are, preferably, aqueous solutions of acrylic acid or methacrylic acid. The aqueous monomer solutions may range from about 10 percent by weight to about 95 percent by weight monomer. Preferably, the aqueous monomer solution is from about 15 percent by weight to about 90 percent by weight monomer and most preferably from about 20 percent to about 65 percent by weight monomer. As the monomer concentration increases, there is an increased risk of undesirable polymer formation when the monomer solution is exposed to ultraviolet radiation.

The levels of impurities in aqueous monomer solutions are reduced by subjecting the aqueous monomer solution containing the impurities to ultraviolet radiation for from about 2 minutes to about 5 hours. The ultraviolet radiation may be produced by any suitable source such as, for example, a mercury vapor lamp. Suitable means for subjecting the aqueous monomer solution containing the carbonyl impurities to ultraviolet radiation include a stationary or stirred sample of aqueous monomer solution in the presence of an ultraviolet light source, and passing or recirculating a stream of the aqueous monomer solution through one or more regions where the stream will be exposed to an ultraviolet light source. Preferably, the aqueous monomer solution containing the carbonyl impurities is subjected to ultraviolet light by passing or recirculating a stream of the aqueous monomer solution through one or more regions where the stream will be exposed to an ultraviolet light source. The aqueous monomer solution is subjected to ultraviolet radiation for from about 2 minutes to about 5 hours, which can be a single continuous exposure or two or more intermittent exposures providing a total average time of exposure of from about 5 minutes to about 5 hours, preferably from about 15 minutes to about 3 hours.

It is known that ultraviolet radiation can initiate polymerization of ethylenically unsaturated monomers. Therefore, it is preferred that the aqueous monomer solution containing the impurities is inhibited with one or more polymerization inhibiting compounds. Polymerization inhibiting compounds are well known to those skilled in the art and include, for example, hydroquinone ("HQ"), hydroquinone monomethyl ether, hydroquinone monoethyl ether, benzoquinone, phenothiazine, and alkylphenols. Preferably, polymerization inhibitors are present in the aqueous monomer solution at a level of from about 20 to about 2,000 parts per million, and preferably from about 100 to about 1,000 parts per million. The preferred level of polymerization inhibitor will increase as the concentration of the monomer solution increases. Certain of these compounds, such as hydroquinone and hydroquinone monomethyl ether, require the presence of oxygen in order to function as polymerization inhibitors. Thus, it is desirable to ensure that oxygen is present in the aqueous monomer solution when using these polymerization inhibitors. Oxygen can be introduced into the aqueous monomer solution, for example, by bubbling, or sparging, air or oxygen into the aqueous monomer solution.

The aqueous monomer solution may be exposed to the ultraviolet radiation at a temperature up to the boiling point of the aqueous monomer solution. Preferably, the aqueous monomer solution may be exposed to the ultraviolet radiation at a temperature of from about 10° C. to about 60° C. This temperature range is preferred because it may not require the aqueous monomer solution resulting from the vapor phase oxidation to be heated or cooled.

The following procedure was used to evaluate the effectiveness of ultraviolet radiation at reducing the levels of various carbonyl-containing impurities present in an aqueous solution of acrylic acid.

To a 300-milliliter four neck flask equipped with a magnetic stirring bar, an air inlet, a thermometer and an exit and a return tube for the recirculation of monomer, was added 60 grams of 28-32 percent by weight aqueous acrylic acid solution, containing from 400-1,000 parts per million ("ppm") of HQ, prepared by vapor phase oxidation of propylene. The protoanemonin (PTA), furfural and benzaldehyde (PhCHO) levels of the aqueous acrylic acid solution were determined by high pressure liquid chromatography (HPLC) and are reported in ppm based on the aqueous monomer solution. The magnetic stirring bar was activated and air was continuously bubbled through the aqueous monomer solution. A 200 Watt, medium pressure, quartz, mercury vapor lamp (available from Ace Glass Co., Vineland, N.J. catalog no. 7825-32) was turned on, and allowed to equilibrate in a photochemical reactor (available from Ace Glass Co., Vineland, N.J. catalog no. 7878). After fifteen minutes, the aqueous acrylic acid solution was continuously pumped though the exit tube into the photochemical reactor and back to the flask through the return tube. An average residence time of 33 seconds was provided by maintaining a constant volume of 20 milliliters of acrylic acid solution in the photochemical reactor and a flow rate of 36.4 milliliters per minute. The levels of furfural, PTA, PhCHO and HQ were measured periodically by HPLC. The temperature of the aqueous acrylic acid solution remained 24° C. The data appear below.

|  | Time (minutes) | Furfural (ppm) | PTA (ppm) | PhCHO (ppm) | HQ (ppm) |
| --- | --- | --- | --- | --- | --- |
| Example 1 | 0 | 62 | 37 | 43 | 1016 |
|  | 180 | 16 | 25 | 31 | 669 |
| Example 2 | 0 | 65 | 39 | 46 | 260 |
|  | 180 | 9 | 22 | 28 | 88 |

|  | Time (minutes) | PTA (ppm) | Furfural (ppm) | PhCHO (ppm) |
| --- | --- | --- | --- | --- |
| Example 3 | 0 | 50 | 69 | 73 |
|  | 30 | 33 | 13 | 63 |
|  | 60 | 29 | 8 | 60 |
|  | 90 | 24 | 7 | 53 |
|  | 120 | 12 | 6 | 44 |
|  | 150 | 5 | 6 | 40 |
|  | 180 | 4 | 7 | 31 |

|  | Time (minutes) | PTA (ppm) | Furfural (ppm) | PhCHO (ppm) |
| --- | --- | --- | --- | --- |
| Example 4* | 0 | 54 | 66 | 74 |
|  | 5 | 50 | 58 | 70 |
|  | 10 | 45 | 47 | 67 |
|  | 20 | 43 | 32 | 61 |
|  | 30 | 38 | 19 | 62 |
|  | 40 | 37 | 14 | 68 |
|  | 50 | 34 | 8 | 63 |
|  | 60 | 35 | 7 | 62 |

|  | Time (minutes) | PTA (ppm) | Furfural (ppm) | PhCHO (ppm) | HQ (ppm) |
| --- | --- | --- | --- | --- | --- |
| Example 5 | 0 | 39 | 64 | 44 | 412 |
|  | 10 | 35 | 48 | 41 | — |
|  | 20 | 34 | 38 | 41 | — |
|  | 30 | 32 | 29 | 41 | — |
|  | 40 | 31 | 22 | 39 | — |
|  | 50 | 29 | 17 | 35 | — |

| | 60 | 29 | 16 | 37 | 257 |

*The initial level of HQ was 500 ppm

The data appearing show the effectiveness of ultraviolet radiation in reducing the level of impurities in aqueous monomer solutions when the aqueous monomer solutions are subjected to ultraviolet radiation.

What is claim is:

1. A method of reducing the level of impurities in an aqueous monomer solution, consisting essentially of: subjecting an impurity-containing aqueous monomer solution consisting essentially of
   (a) from about 10% to about 95 percent by weight of monomer;
   (b) water; and
   (c) impurities including carbonyl compound impurities;
to ultraviolet radiation for from about 2 minutes to about 5 hours to reduce the level of the carbonyl compound impurities by at least 5 percent based on the amount of carbonyl compound impurities in the impurity-containing aqueous monomer solution without unwanted polymer formation.

2. The method of claim 1, wherein the aqueous monomer solution is an aqueous solution of acrylic acid.

3. The method of claim 1, wherein the aqueous monomer solution is an aqueous solution of methacrylic acid.

4. The method of claim 1, wherein the impurities are selected from acrolein, methacrolein, acetaldehyde, furfural, protoanemonin, formaldehyde, crotonaldehyde, acetone and benzaldehyde.

5. A method of reducing the level of impurities in an aqueous monomer solution, consisting essentially of: subjecting an impurity-containing aqueous monomer solution consisting essentially of
   (a) from about 10 to about 95 percent by weigh of a monomer selected from the group consisting of acrylic acid and methacrylic acid,
   (b) water and
   (c) impurities including carbonyl compound impurities selected from the group consisting of acrolein, methacrolein, acetaldehyde, furfural, protoanemonin, formaldehyde, crotonaldehyde, acetone and benzaldehyde
to ultraviolet radiation for from about 2 minutes to about 5 hours to reduce the level of the carbonyl compound impurities by at least 5 percent based on the amount of carbonyl compound impurities in the impurity-containing aqueous monomer solution without unwanted polymer formation.

6. The method of claim 4 or claim 5, wherein the impurities are selected from furfural, protoanemonin and benzaldehyde.

7. The method of claim 1 or claim 5 wherein the impurity-containing aqueous monomer solution is subjected to ultraviolet radiation for from about 5 minutes to about 3 hours.

8. The method of claim 1 or claim 5, wherein the impurity-containing aqueous monomer solution is subjected to ultraviolet radiation for from about 2 minutes to about 5 hours via a single continuous exposure to the ultraviolet radiation.

9. The method of claim 1 or claim 5, wherein the impurity-containing aqueous monomer solutions subjected to ultraviolet radiation for from about 2 minutes to about 5 hours via at least two intermittent exposures to the ultraviolet radiation.

10. The method of claim 1 or claim 5, wherein the impurity-containing aqueous monomer solution is subjected to ultraviolet radiation in the presence of at least one polymerization inhibitor and oxygen.

* * * * *